United States Patent
Serita

(10) Patent No.: US 6,766,272 B2
(45) Date of Patent: Jul. 20, 2004

(54) METHOD AND APPARATUS FOR DERIVING BODY FAT AREA

(75) Inventor: Eiichi Serita, Akita (JP)

(73) Assignee: Tanita Corporation, Tokyo (JP)

( * ) Notice: Subject to any disclaimer, the term of this patent is extended or adjusted under 35 U.S.C. 154(b) by 255 days.

(21) Appl. No.: 09/983,426

(22) Filed: Oct. 24, 2001

(65) Prior Publication Data

US 2002/0052697 A1 May 2, 2002

(30) Foreign Application Priority Data

Oct. 27, 2000 (JP) ........................................ 2000-328687
Dec. 26, 2000 (JP) ........................................ 2000-394515

(51) Int. Cl.$^7$ .............................................. G01B 21/28
(52) U.S. Cl. ..................................... 702/156; 702/155
(58) Field of Search ................................ 702/155, 156, 702/173

(56) References Cited

U.S. PATENT DOCUMENTS

| | | | |
|---|---|---|---|
| 5,579,782 A | * 12/1996 | Masuo | 600/547 |
| 5,628,328 A | 5/1997 | Nissen et al. | |
| 6,088,615 A | 7/2000 | Masuo | |
| 6,123,451 A | 9/2000 | Schaefer et al. | |
| 6,487,445 B1 | 11/2002 | Serita et al. | |

FOREIGN PATENT DOCUMENTS

| | | | |
|---|---|---|---|
| EP | 0 865 763 | 9/1998 | |
| JP | 10-192258 | * 7/1998 | ........... A61B/5/107 |
| WO | WO 9608198 | 3/1996 | |
| WO | WO98/08088 | 2/1998 | |
| WO | WO 00/28897 | 8/2000 | |

OTHER PUBLICATIONS

"Abdominal Fat Depots Measured With Computed Tomography: Effects of Degree of Obesity, Sex, and Age", J. C. Seidell et al., European Journal of Clinical Nutrition (1988), vol. 42, pp. 805–815.

* cited by examiner

Primary Examiner—John Barlow
Assistant Examiner—Douglas N Washburn
(74) Attorney, Agent, or Firm—McDermott Will & Emery LLP

(57) ABSTRACT

An apparatus for deriving a body fat area comprises a parameter measuring unit and/or a parameter input unit, an arithmetic unit and a display unit. The parameter measuring unit measures a parameter value correlated to the body fat area, including a subcutaneous fat area and a visceral fat area, and the parameter input unit enters a parameter value correlated to the body fat area. The arithmetic unit calculates the subcutaneous and visceral body fat area from the measured parameter value and/or from the input parameter value by using a regression equation. The display unit displays for the calculated subcutaneous and visceral fat areas in a concentric circle format.

19 Claims, 14 Drawing Sheets

Visceral Fat Area (CT Area and Calculated Area)

Calculated Area(=c65 x trunk segument fat mass + f65)

Visceral Fat Area (CT Area and Calculated Area)

Calculated Area(=a59 x girth of abdomen + f59)

Visceral Fat Area (CT Area and Calculated Area)

Calculated Area(=a62 x girth of abdomen + d62 x age + f62)

Visceral Fat Area (CT Area and Calculated Area)

Calculated Area(=a55 x girth of abdomen + b55 x BMI
+ c55 x whole body fat mass + f55)

Visceral Fat Area (CT Area and Calculated Area)

Calculated Area(=a58 × girth of abdomen + b58 × BMI + c58 × whole body fat mass + d58 × age + f58)

Comment Window "A"

| Continue the current living condition |
|---|

Comment Window "B"

Select any one of the followings and do an exercise
1. Jogging for 30 min/day, 4 days/week,
   for 3 months
2. Walking in water for 30 min/day, 2 days/week,
   for 5 months

METHOD AND APPARATUS FOR DERIVING BODY FAT AREA

BACKGROUND OF THE INVENTION

1. Field of the Invention

The present invention generally relates to a method and an apparatus for deriving a body fat area that is an information useful for health care, and more particularly, to a method and an apparatus for deriving a body fat area by which one can know a visceral fat area and a subcutaneous fat area.

2. Prior Arts

A various types of measuring apparatus have been known for measuring body fat of a person that is a major factor for corpulence. For example, Japanese Patent No. 1848283 discloses a body fat weight meter in which sex, height and age of a person are entered; body weight and impedance between extreme portions of the body are measured; and fat tissue weight in the body is estimated. Another example is an MRI or X-ray CT apparatus for taking a tomographic picture for an abdomen (in particular a navel region) of the body and deriving subcutaneous fat area and visceral fat area based on the result of picture analysis.

It is well known that there are two types of corpulence: subcutaneous fat type and visceral fat type. Recently it has become more important to know the visceral fat mass that greatly affects the cause of suffering from adult noncommunicable disease, and therefore, it is desired to determine whether the corpulence is subcutaneous fat type or visceral fat type.

However, the prior art apparatus as described above have several problems as follows: In the body fat weight meter one can only know whole body fat mass or whole percent fat. On the other hand, the MRI or X-ray CT apparatus is very expensive. Such apparatus needs some expert operator for letting a person to be measured lay down and kept at that position during the measurement. The apparatus is difficult to operate by an ordinary person alone, and therefore, it is not suitable for home use. In addition, the apparatus is bulky and cumbersome to handle, and takes longer period of time for measurement. More importantly, in the measurement with the X-ray CT apparatus, a person to be measured is exposed to X-ray that is very small amount and not to impair the health, but the person to be measured does not spontaneously undergo the measurement from the psychological point of view. In this connection, the measurement with the X-ray CT apparatus should not repeatedly be conducted to the same person because of accumulation of X-ray exposure.

Furthermore, in the past, a subcutaneous fat area and a visceral fat area have been derived in such manner that a tomographic picture for an abdomen (in particular a navel region) of a human body is taken by use of an X-ray CT apparatus and the picture is analyzed to produce numerical data. Thereafter, an expert person such as a physician evaluates the subcutaneous fat area and the visceral fat area based on the numerical data produced and gives an advice to a person under test according to the result of evaluation.

However, in view of the fact that the measurement result of the subcutaneous fat area and the visceral fat area is represented simply by the numerical data at the time when it is derived, it is difficult to determine whether such measurement result of the subcutaneous fat area and the visceral fat area is good for the health or it requires some health care unless reference to a separate evaluation criterion is made. In addition, an advice by an expert person such as a physician or reference to a guidance book is necessary in order to successfully perform the health care in future in response to the measurement result. In any way, the prior art apparatus is defective in that a person under test can't easily understand own health condition.

In view of the above an object of the present invention is to provide a method and an apparatus for easily deriving a body fat area while solving the above-mentioned prior art problems.

SUMMARY OF THE INVENTION

To attain such object the present invention provides a method for deriving a body fat area, comprising the steps of: measuring a parameter value correlated to the body fat area; and calculating the body fat area from the measured parameter value by using a regression equation for estimation of the body fat area based on the measured parameter value.

According to one embodiment of the present invention said parameter value correlated to the body fat area includes a value for any one of, or any combination of, the followings: whole body fat, trunk segment fat, girth of an abdomen, corpulence evaluation index and body weight.

According to another embodiment of the present invention said body fat area is represented by a value for any one of the followings: visceral fat, subcutaneous fat and gross fat.

According to further embodiment of the present invention said value for visceral fat is the value for the area of visceral fat, said value for subcutaneous fat is the value for the area of subcutaneous fat, and said value for gross fat is the value for the area of gross fat.

According to yet further embodiment of the present invention said step of calculating the body fat area from the measured parameter value takes into consideration of personal data including sex, age, height, race, etc.

In another aspect, the present invention provides an apparatus for deriving a body fat area, comprising: a parameter measuring unit and/or a parameter input unit; and an arithmetic unit, whereby, said parameter measuring unit measures a parameter value correlated to the body fat area and said parameter input unit enters a parameter value correlated to the body fat, and said an arithmetic unit calculates the body fat area from the measured parameter value obtained by said parameter measuring unit and/or from the input parameter value entered by said parameter input unit, by using a regression equation for estimation of the body fat area based on said measured parameter value and said input parameter value.

According to one embodiment of the present invention said parameter value correlated to the body fat area includes a value for any one of, or any combination of, the followings: whole body fat, trunk segment fat, girth of abdomen, corpulence evaluation index and body weight.

According to another embodiment of the present invention said body fat area is represented by a value for any one of the followings: visceral fat, subcutaneous fat and gross fat.

According to further embodiment of the present invention said value for visceral fat is the value for the area of visceral fat, said value for subcutaneous fat is the value for the area of subcutaneous fat, and said value for gross fat is the value for the area of gross fat.

According to yet further embodiment of the present invention said apparatus further includes a personal data input unit, whereby said personal data input unit enters a personal data including sex, age, height, race, etc., and said arithmetic unit takes into consideration of the personal data entered by said personal data input unit.

According to yet further embodiment of the present invention said apparatus further includes a personal data measuring unit, whereby said personal data measuring unit measures a personal data including sex, age, height, race, etc., and said arithmetic unit takes into consideration of the personal data measured by said personal data measuring unit.

According to yet further embodiment of the present invention said apparatus further includes a personal data input unit and a personal data measuring unit, whereby said personal data input unit enters the personal data including sex, age, height, race, etc., and said personal data measuring unit measures the personal data including sex, age, height, race, etc., and said arithmetic unit takes into consideration of the personal data entered by said personal data input unit and measured by said personal data measuring unit.

According to yet further embodiment of the present invention said apparatus further includes a memory unit, whereby said memory unit stores the regression equation for estimation of the body fat area, and said arithmetic unit calculates the body fat area by using the regression equation for estimation of the body fat area stored in said memory unit.

According to yet further embodiment of the present invention said apparatus further includes an evaluation unit, whereby said evaluation unit evaluates the health or corpulence condition based upon the result of the body fat area derived by the arithmetic unit.

According to yet further embodiment of the present invention said apparatus further includes a display unit, whereby said display unit displays the results produced by the arithmetic unit and the evaluation unit.

According to yet further embodiment of the present invention a measuring unit for measuring the girth of abdomen includes an encoder type measure.

According to yet further embodiment of the present invention the measuring unit for measuring the girth of abdomen includes an ultrasonic type measure.

In further aspect, the present invention provides an apparatus for deriving a body fat area, comprising: an evaluation unit; and a display unit, whereby, said evaluation unit evaluates the result of body fat area derived and produces an evaluation criterion and/or advice information about corpulence or health condition, and said display unit displays said evaluation criterion and/or advice information produced by said evaluation unit.

According to one embodiment of the present invention said apparatus further comprises: a parameter measuring unit and/or a parameter input unit; a memory unit; and an arithmetic unit, whereby, said parameter measuring unit measures a parameter value correlated to the body fat area, and said parameter input unit enters a parameter value correlated to the body fat area, said memory unit stores a regression equation for estimation of the body fat area; and said arithmetic unit calculates the body fat area based on said parameter values from said parameter measuring unit and/or said parameter input unit by using said regression equation for estimation of the body fat area stored in said memory unit.

According to another embodiment of the present invention said apparatus further comprises a personal data input unit and/or a personal data measuring unit, whereby said personal data input unit enters a personal data including sex, age and height, and said personal data measuring unit measures a personal data including sex, age and height, and said arithmetic unit takes into consideration of the personal data from said personal data input unit and/or said personal data measuring unit.

According to further embodiment of the present invention said display unit displays a graph having an evaluation criterion for evaluating a relationship between said body fat area and other living body information.

According to yet further embodiment of the present invention said body fat area is represented by a value for visceral fat, subcutaneous fat or gross fat.

According to yet further embodiment of the present invention said evaluation criterion includes threshold lines.

According to yet further embodiment of the present invention said threshold lines are successively provided.

According to yet further embodiment of the present invention a display pattern is changed for each of regions defined by said threshold lines.

According to yet further embodiment of the present invention said display pattern is formed by shape, color, figure, marking, hue and flashing condition.

According to yet further embodiment of the present invention said other living body information includes corpulence evaluation index.

According to yet further embodiment of the present invention said corpulence evaluation index includes Body Mass Index (BMI).

According to yet further embodiment of the present invention said display unit displays a historical graph representing a historical data of the measurement result of the body fat area up to now.

According to yet further embodiment of the present invention said advice information includes a selectable exercise instruction.

According to yet further embodiment of the present invention said body fat area includes a visceral fat area, and said evaluation criterion includes threshold lines provided on the positions where the visceral fat area is 100 $cm^2$ and 130 $cm^2$.

BRIEF DESCRIPTION OF THE ACCOMPANYING DRAWINGS

Now, the present invention will be described in more detail with reference to the accompanying drawings, in which.

DESCRIPTION OF THE PREFERRED EMBODIMENTS

Figure 1:
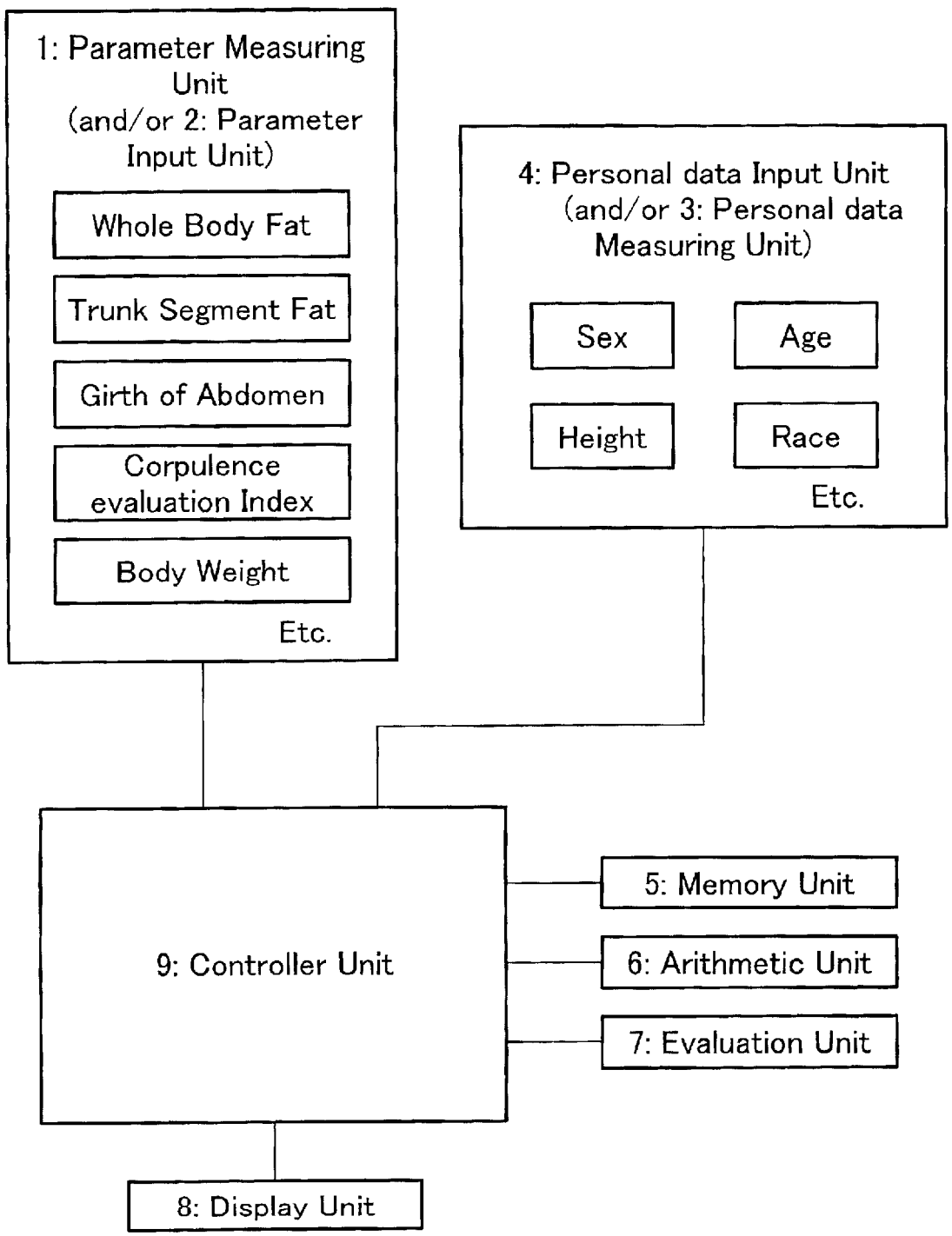
FIG. 1 is a schematic block diagram illustrating an apparatus for deriving a body fat area according to the present invention.

FIG. 1 is a schematic block diagram illustrating an apparatus for deriving a body fat area according to the present invention. The apparatus for deriving the body fat area includes a parameter measuring unit 1 for measuring parameter values correlated to the body fat area; a personal data input unit 4 for entering personal data including sex, age, height, race, etc.; a memory unit 5 for storing a regression equation for estimation of the body fat area; an arithmetic unit 6 for calculating the body fat area based on the data from the parameter measuring unit 1 and the personal data input unit 4 by using the regression equation for estimation of the body fat area stored in the memory unit 5; an evaluation unit 7 for evaluating the health or corpulence condition based on the result of the body fat area from the arithmetic unit 6; a display unit 8 for displaying the results from the arithmetic unit 6 and the evaluation unit 7; and a controller unit 9 for controlling the operation of said units.

The controller unit 9 receives the data from the parameter measuring unit 1 and the personal data input unit 4; transfers them to the arithmetic unit 6 for calculating the body fat area using the regression equation stored in the memory unit 5; operates the evaluation unit 7 for evaluating the health and corpulence condition based on the result of the body fat area from the arithmetic unit 6; and operates the display unit 8 for displaying the results from the arithmetic unit 6 and the evaluation unit 7.

The parameter value correlated to the body fat area and measured by the parameter measuring unit 1 is any one of the followings: whole body fat, trunk segment fat, girth of abdomen, corpulence evaluation index and body weight. Of course, any combination of more than two of them may be used as the parameter. Each of those parameters directly correlates to the body fat area.

The term "whole body fat" as used herein means the percent fat of whole body, body fat mass of whole body, etc. The term "trunk segment fat" means the percent fat of trunk segment, body fat mass of trunk segment, etc. In addition, the term "corpulence evaluation index" means an index over which a person is determined as being corpulent, which is derived from a ratio of body weight and height of the person. For example, the corpulence evaluation index includes the followings: Body Mass Index (BMI) that is derived by an equation "body weight (kg)÷height (m)÷height (m)"; Kaup Index that is derived by an equation "body weight (kg)÷height (m)÷height (m)×$10^4$"; and Rohrer Index that is derived by an equation "body weight (kg)÷height (m)÷height (m)÷height (m)×$10^7$".

The term "personal data" means sex, age, height, race, etc., of a person to be measured. Such parameter does not directly correlate to the body fat area, but becomes correlated thereto if it is combined with some other parameter that is correlated to the body fat area.

The term "body fat area" means any one of, or any combination of, the followings: a value for visceral fat represented by visceral fat area, visceral fat mass, visceral percent fat, etc.; a value for subcutaneous fat represented by subcutaneous fat area, subcutaneous fat mass, subcutaneous percent fat, etc.; and a value for gross fat represented by gross fat area, gross fat mass, gross percent fat, etc. that is the sum of visceral fat and subcutaneous fat.

The term "visceral fat area" means a visceral area in the cross section passing through an abdomen (mainly a navel region) of a body. The term "subcutaneous fat area" means a subcutaneous area in the cross section passing through an abdomen (mainly a navel region) of a body.

Now, a method for deriving a body fat area according to the present invention will be described in more detail in conjunction with the operation of the apparatus as described above.

Figure 2:
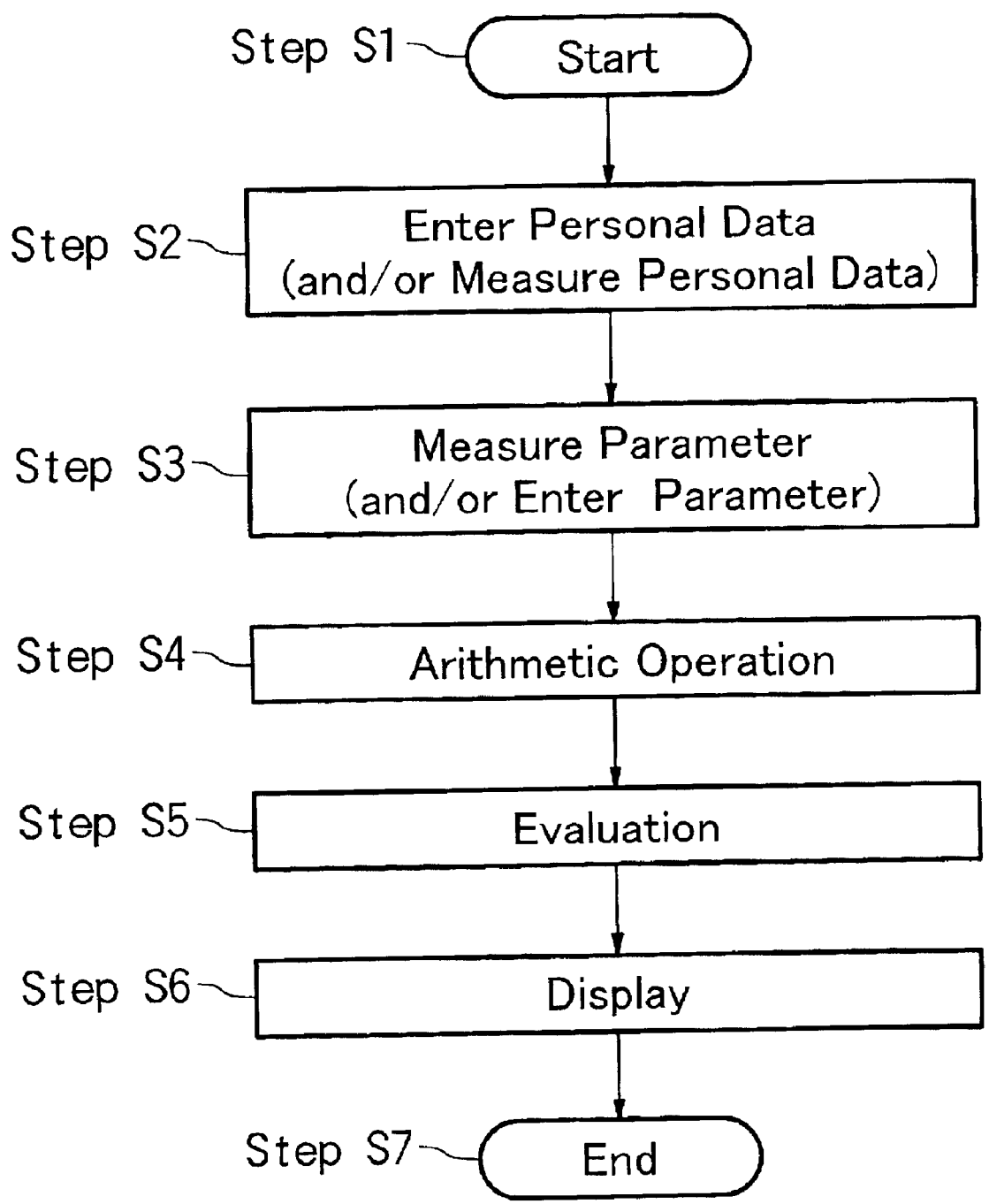
FIG. 2 is a flow chart illustrating a sequence of steps for deriving a body fat area.

FIG. 2 is a flow chart illustrating a sequence of steps for deriving a body fat area. First of all, the apparatus for deriving the body fat area is turned ON (Step S1). Then, the personal data including sex, age, height, race, etc. are entered by use of the personal data input unit 4 (Step S2). Thereafter, the parameter measuring unit 1 is operated to measure the parameter values correlated to the body fat area, such as whole body fat, trunk segment fat, girth of an abdomen, corpulence evaluation index, and body weight (Step S3).

Then, the arithmetic unit 6 is operated to calculate the body fat area, as described latter in more detail, by using the regression equation for estimation of the body fat area based on the personal data entered by the personal data input unit 4 and stored in the memory unit 5 and the parameter values measured by the parameter measuring unit 1 (Step S4). Next, the evaluation unit 7 is operated for evaluating the health or corpulence condition based upon the result of the body fat area produced by the arithmetic unit 6 (Step S5). The result of the body fat area produced by the arithmetic unit 6 and the result of evaluation by the evaluation unit 7 are displayed on the display unit 8 (Step S6). Finally a person to be measured can see the results, and then, the operation is ended (Step S7).

Figure 3:
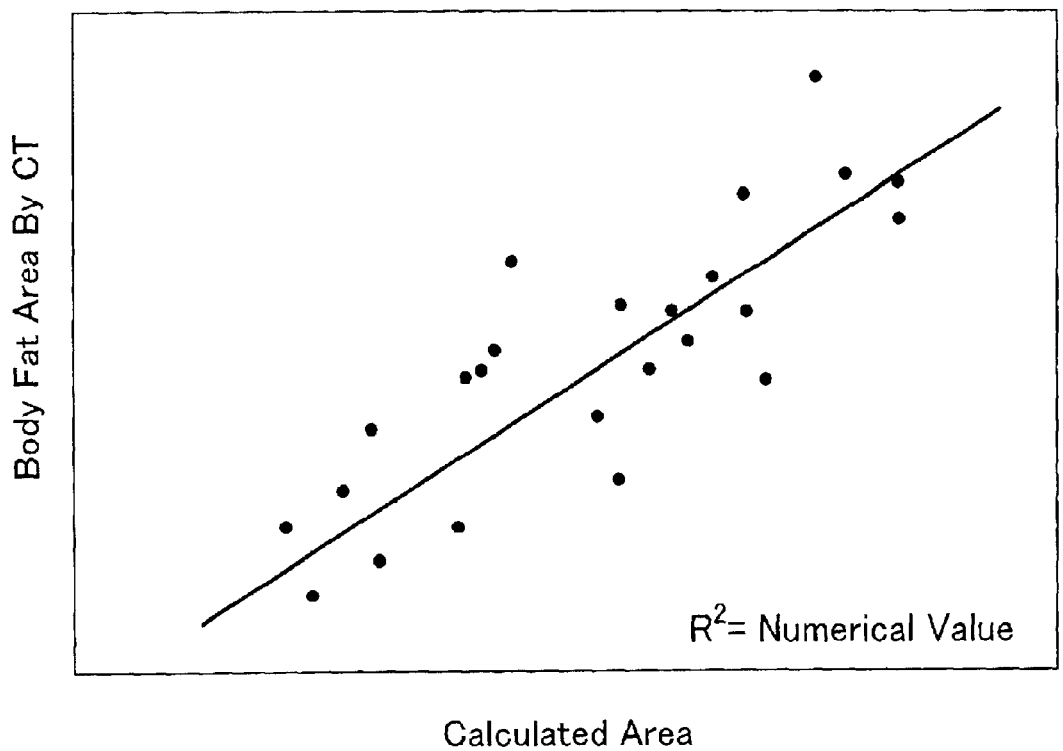
FIG. 3 is a graph showing correlation between a body fat area produced by an X-ray CT apparatus and a body fat area calculated by using the regression equation for estimation of the body fat area based upon the parameter values.

FIG. 3 is a graph showing correlation between a body fat area CT produced by an X-ray CT apparatus and a body fat area calculated by using the regression equation for estimation of the body fat area based upon the parameter values. Referring to FIG. 3, the ordinate of the graph plots the body fat area produced by the X-ray CT apparatus and the abscissa plots the calculated body fat area produced by using the regression equation. A straight line represents a regression line, and dots represent sampled data on the bases of which the regression line is created. In addition, "$R^2$" is a coefficient of determination in the range of $0 \leq R^2 \leq 1$. $R^2$ approaching 1 means that there is less difference between the data and the regression line so that the regression line is well fitted to the sampled data.

In this manner it has been found that there is correlation present between the body fat area produced by the X-ray CT apparatus and the calculated body fat area produced by using the regression equation for estimation of the body fat area based upon the parameter values. The more concrete data that shows the correlation between the body fat area by CT and the calculated area in FIG. 3 are illustrated in FIGS. 4 to 11.

Figure 4:
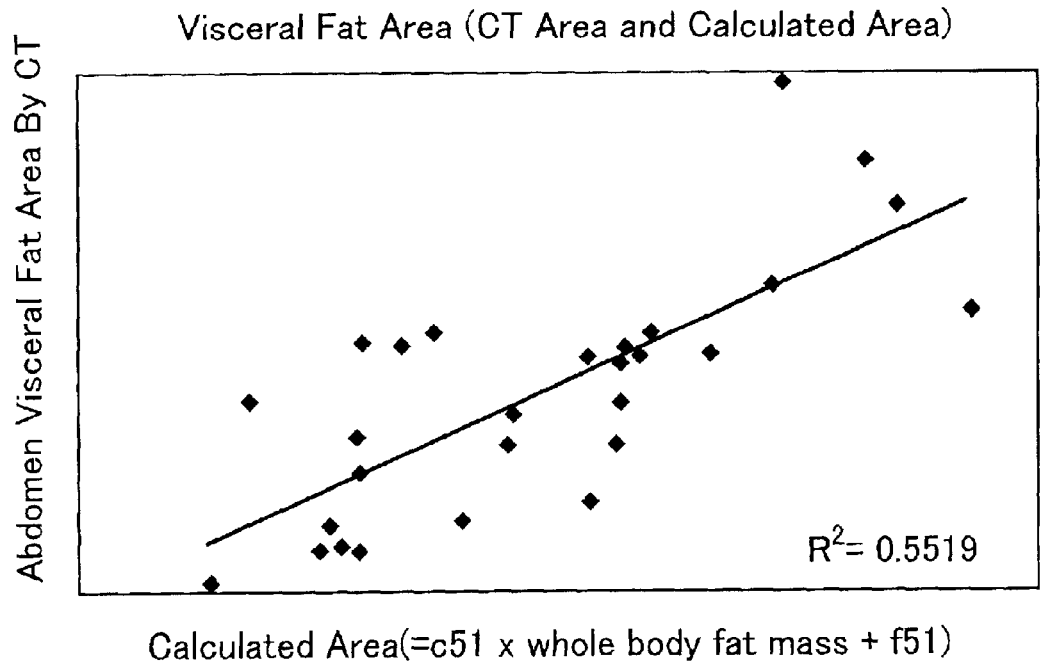
FIG. 4 is a graph illustrating correlation between a visceral fat area produced by the X-ray CT apparatus, as plotted on the ordinate, and a calculated area produced by using the regression equation for estimation of the visceral fat area based upon whole body fat mass, as plotted on the abscissa.
Figure 5:
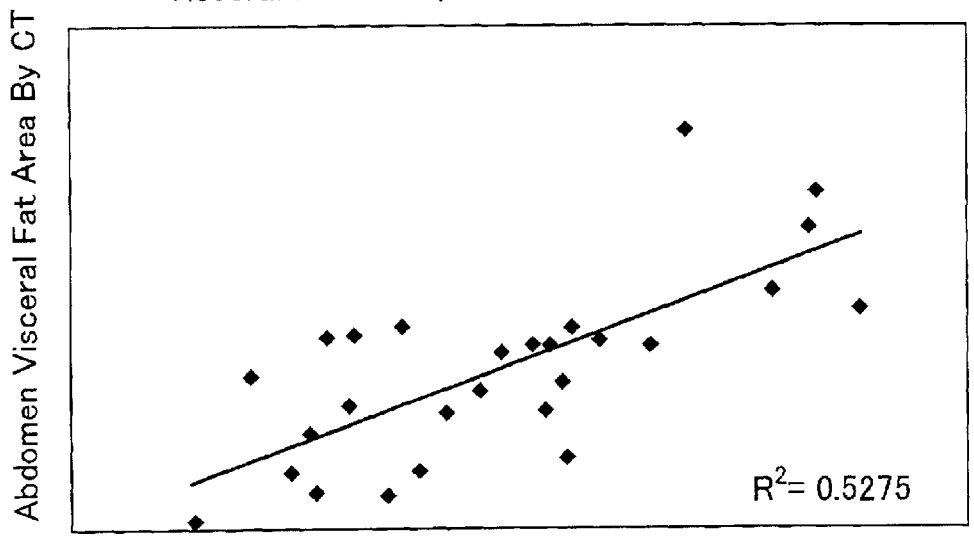
FIG. 5 is a graph illustrating correlation between a visceral fat area produced by the X-ray CT apparatus, as plotted on the ordinate, and a calculated area produced by using the regression equation for estimation of the visceral fat area based upon trunk segment fat mass, as plotted on the abscissa.
Figure 6:
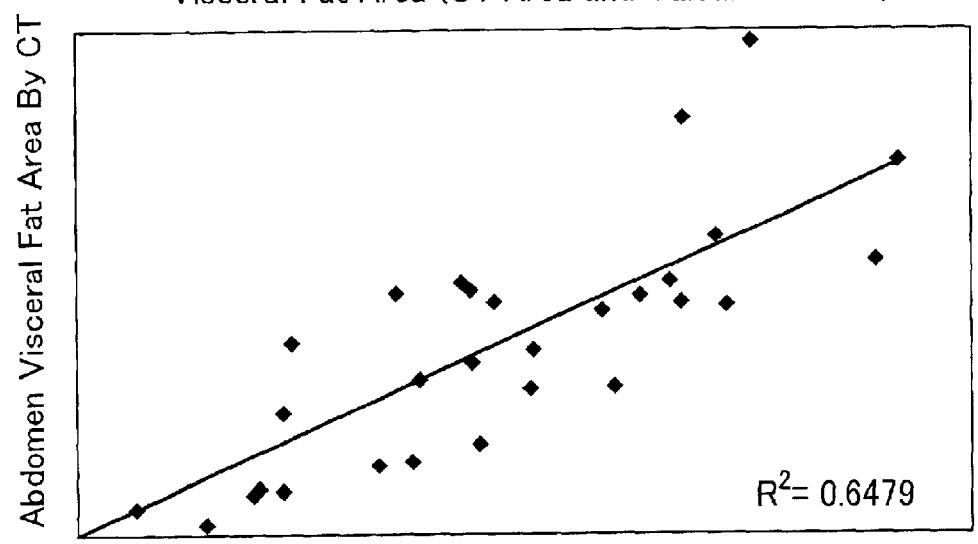
FIG. 6 is a graph illustrating correlation between a visceral fat area produced by the X-ray CT apparatus, as plotted on the ordinate, and a calculated area produced by using the regression equation for estimation of the visceral fat area based upon girth of an abdomen, as plotted on the abscissa.
Figure 7:
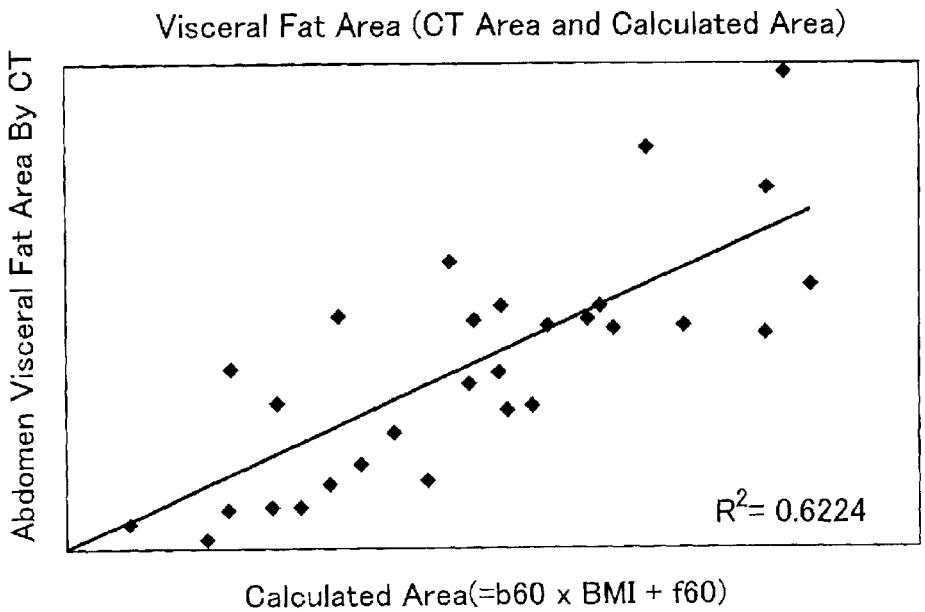
FIG. 7 is a graph illustrating correlation between a visceral fat area produced by the X-ray CT apparatus, as plotted on the ordinate, and a calculated area produced by using the regression equation for estimation of the visceral fat area based upon BMI, as plotted on the abscissa.
Figure 8:
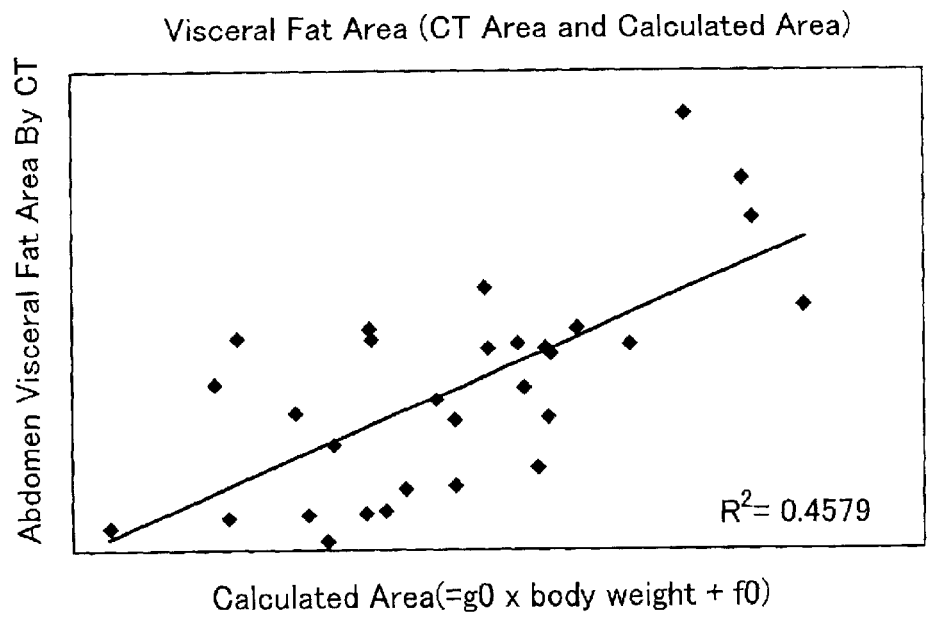
FIG. 8 is a graph illustrating correlation between a visceral fat area produced by the X-ray CT apparatus, as plotted on the ordinate, and a calculated area produced by using the regression equation for estimation of the visceral fat area based upon body weight, as plotted on the abscissa.
Figure 9:
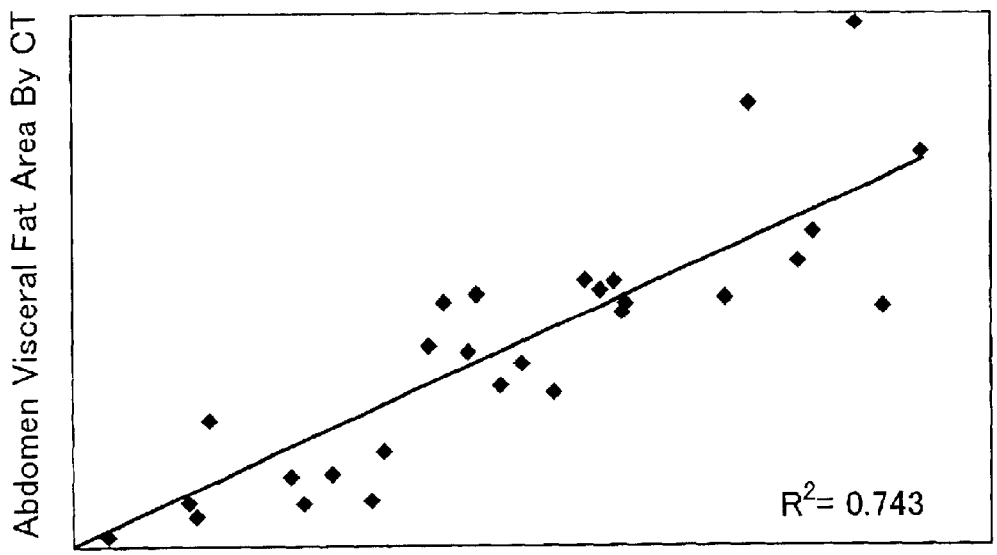
FIG. 9 is a graph illustrating correlation between a visceral fat area produced by the X-ray CT apparatus, as plotted on the ordinate, and a calculated area produced by using the regression equation for estimation of the visceral fat area based upon girth of an abdomen and age, as plotted on the abscissa.
Figure 10:
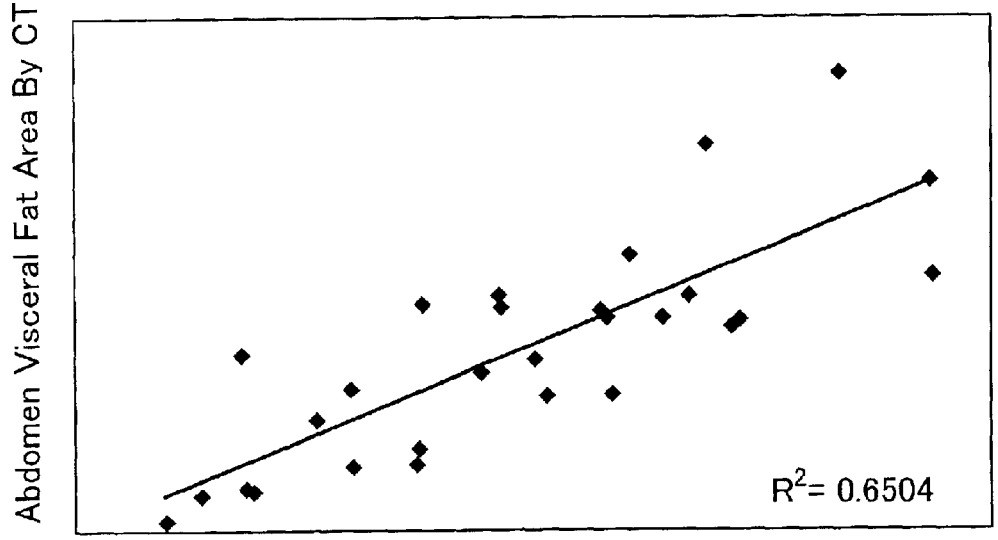
FIG. 10 is a graph illustrating correlation between a visceral fat area produced by the X-ray CT apparatus, as plotted on the ordinate, and a calculated area produced by using the regression equation for estimation of the visceral fat area based upon girth of an abdomen, BMI and whole body fat mass, as plotted on the abscissa.
Figure 11:
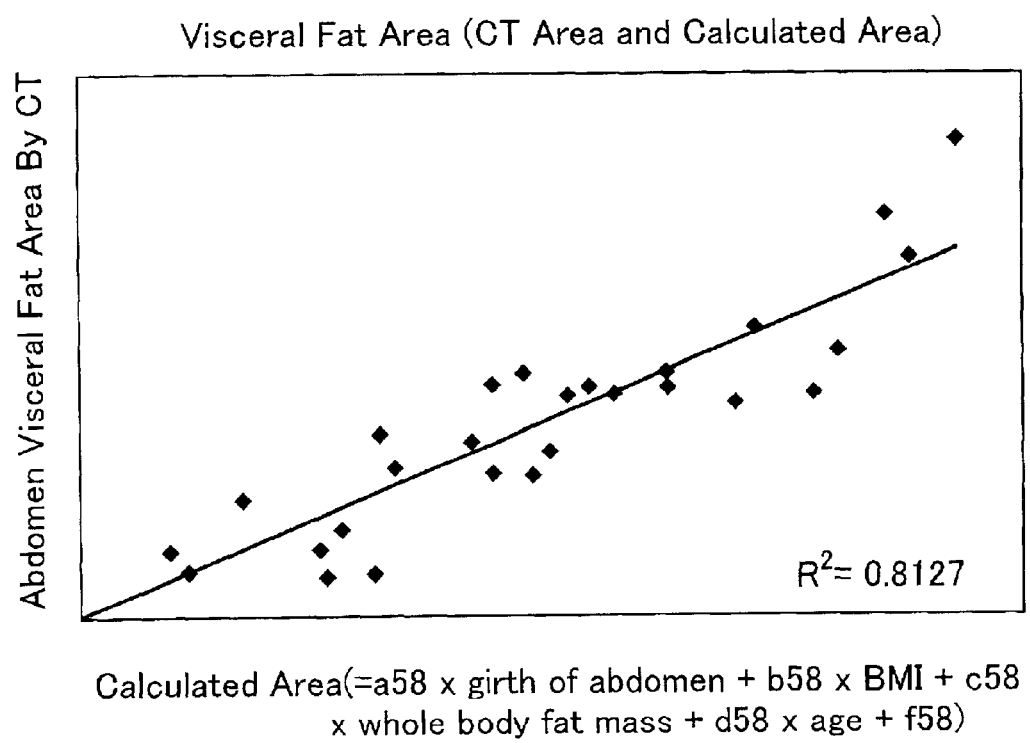
FIG. 11 is a graph illustrating correlation between a visceral fat area produced by the X-ray CT apparatus, as plotted on the ordinate, and a calculated area produced by using the regression equation for estimation of the visceral fat area based upon girth of an abdomen, BMI, whole body fat mass and age, as plotted on the abscissa.

FIG. 4 is a graph illustrating the correlation between a visceral fat area produced by the X-ray CT apparatus, as plotted on the ordinate, and a calculated area produced by using the regression equation for estimation of the visceral fat area based upon whole body fat mass, as plotted on the abscissa. FIG. 5 is a graph illustrating the correlation between a visceral fat area produced by the X-ray CT apparatus, as plotted on the ordinate, and a calculated area produced by using the regression equation for estimation of the visceral fat area based upon trunk segment fat mass, as plotted on the abscissa. FIG. 6 is a graph illustrating the correlation between a visceral fat area produced by the X-ray CT apparatus, as plotted on the ordinate, and a calculated area produced by using the regression equation for estimation of the visceral fat area based upon girth of an abdomen, as plotted on the abscissa. FIG. 7 is a graph illustrating the correlation between a visceral fat area produced by the X-ray CT apparatus, as plotted on the ordinate, and a calculated area produced by using the regression equation for estimation of the visceral fat area based upon BMI, as plotted on the abscissa. FIG. 8 is a graph illustrating the correlation between a visceral fat area produced by the X-ray CT apparatus, as plotted on the ordinate, and a calculated area produced by using the regression equation for estimation of the visceral fat area based upon body weight, as plotted on the abscissa. FIG. 9 is a graph illustrating the correlation between a visceral fat area produced by the X-ray CT apparatus, as plotted on the ordinate, and a calculated area produced by using the regression equation for estimation of the visceral fat area based upon girth of an abdomen and age, as plotted on the abscissa. FIG. 10 is a graph illustrating the correlation between a visceral fat area produced by the X-ray CT apparatus, as plotted on the ordinate, and a calculated area produced by using the regression equation for estimation of the visceral fat area based upon girth of an abdomen, BMI and whole body fat mass, as plotted on the abscissa. FIG. 11 is a graph illustrating the correlation between a visceral fat area produced by the X-ray CT apparatus, as plotted on the ordinate, and a calculated area produced by using the regression equation for estimation of the visceral fat area based upon girth of an abdomen, BMI, whole body fat mass and age, as plotted on the abscissa.

FIGS. 4 to 11 represent some exemplary cases, but there may be so many cases in which correlation is present between the visceral fat area produced by the X-ray CT apparatus and the calculated area produced by using the regression equation for estimation of the visceral fat area based upon any combination of various parameter values.

In the examples of FIGS. 4 to 11 the correlation with the visceral fat area produced by the X-ray CT apparatus was shown, but any apparatus other than the X-ray CT apparatus, such as MRI may be used to produce the visceral fat area with which the correlation is shown. In addition, the correlation with the visceral fat area was shown, but the correlation with any body fat area other than the visceral fat area may be shown.

According to the present invention, for the parameter values to be measured, such as whole body fat, trunk segment fat, girth of an abdomen, corpulence evaluation index and body weight, the value for the coefficient of determination "$R^2$" as shown in the graph is practically sufficient in view of the correlation with the body fat area.

On the other hand, for the personal data such as sex, age, height and race, an experiment has shown that the value for the coefficient of determination "$R^2$" becomes larger due to the combination with some parameters that directly correlate to the body fat area, and such coefficient of determination can be used for more precise estimation of the body fat area.

Now, an arithmetic operation for deriving the body fat area by the arithmetic unit 6 will be described in detail. The arithmetic unit 6 operates to calculate the body fat area by using the regression equation for estimation of the body fat area based on the parameter values, which regression equation is stored in the memory unit 5 and is correlated to the body fat area produced by the X-ray CT apparatus, as shown in FIG. 3. The regression equation for estimation of the body fat area based on the parameter values is written by the following equation (1):

$$Y = a \times X_1 + b \times X_2 + c \times X_3 \ldots y \times X_n + z \qquad (1)$$

According to the equation (1) the estimated value for the body fat area is calculated based upon the personal data entered by the personal data input unit and the parameter values measured by the parameter measuring unit. In the regression equation represented by the equation (1), "Y" is the estimated or calculated value for the body fat area; "$X_1$, $X_2$, $X_3$, ... $X_n$", are parameter values, and "a, b, c, ... z" are coefficients.

In this connection the personal data does not directly form any variable "$X_n$" in the equation (1), but it may be used to form another variable that is correlated to the body fat area. For example, the personal data "height" may be combined with the parameter "weight" that is correlated to the body fat area to form the parameter BMI that is correlated to the body fat area.

In this way, in the method and apparatus for deriving the body fat area according to the present invention, the parameter values such as whole body fat, trunk segment fat, girth of an abdomen, corpulence evaluation index and body weight that correlate to the body fat area are measured by use of the parameter measuring unit 1. Then, the arithmetic unit 6 operates based upon the measured parameter values by using the regression equation for estimation of the body fat area stored in the memory unit 5 to produce the body fat area.

In addition, by taking into consideration of the personal data such as sex, age, height and race that are entered by the personal data input unit 4, a reliable value for the body fat area can be derived with higher precision where the coefficient of determination $R^2$ nearly equals 1.

Furthermore, the evaluation unit 7 evaluates the health or corpulence condition based upon the result of the body fat area produced by the arithmetic unit 6, and the display unit 8 displays the result of evaluation. Accordingly, the person to be measured is prompted to pay more attention about the health or corpulence condition, if necessary. For example, it has been said that the visceral fat type corpulence has more significant effect on the adult noncommunicable disease such as diabetes than the subcutaneous fat type corpulence. Then, if a ratio of visceral fat area/subcutaneous fat area is not less than 0.4, it is determined that there is the visceral fat type corpulence and such result is displayed. On the other hand, if the ratio is less than 0.4, it is determined that there is the subcutaneous fat type corpulence and such result is displayed. Alternatively, if the visceral fat area is not less than 100 cm$^2$, it is determined that there is the visceral fat type corpulence and such result is displayed. In this way the person knows his own corpulence condition and he can takes care of his health if he is under visceral fat type corpulence condition.

In the embodiment as described above the parameter measuring unit 1 and the personal data input unit 4 were used for the data acquisition means for collecting the data on the bases of which the body fat area is estimated. Alternatively, a parameter input unit 2 for entering some parameter values correlated to the body fat area and a personal data measuring unit 3 for measuring personal data such as sex, age, height and race may be used.

In other words, an alternative configuration of the data acquisition means for collecting the data may be implemented for the same purpose so that it includes at least either one of, or both of, the parameter measuring unit 1 and the parameter input unit 2, and additionally, either one of, or both of, the personal data input unit 4 and the personal data measuring unit 3.

Furthermore, in the embodiment as described above, the memory unit 5 was used for storing the regression equation for estimation of the body fat area. Alternatively, another configuration in which a separate storage means such as an IC card is installed may be implemented for the same purpose.

Now, more concrete embodiments according to the present invention will be described with reference to the drawings.

Figure 12:
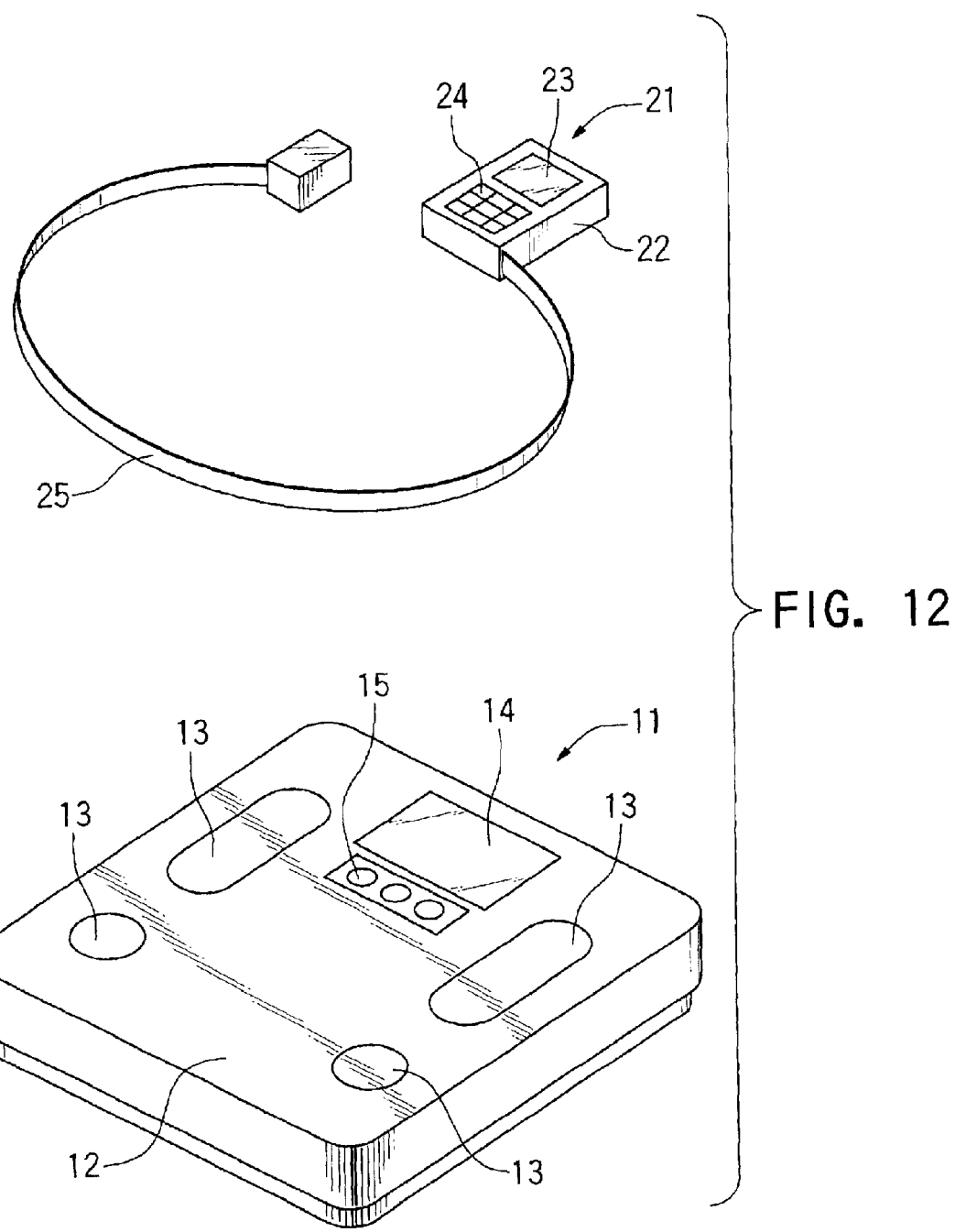
FIG. 12 is a perspective view illustrating one embodiment of an apparatus for deriving a visceral fat area.

FIG. 12 is a perspective view illustrating one embodiment of an apparatus for deriving a visceral fat area. The apparatus for deriving the visceral fat area in this embodiment generally includes a body fat meter with a weight meter 11 and an encoder type measure 21, both of which are connected to each other via a cable (not shown).

The body fat meter with the weight meter 11 corresponds to the parameter measuring unit 1 as described above for measuring whole body fat and body weight. It includes, on an upper surface of an external platform 12, electrodes 13 for detecting whole body impedance, a display unit 14 for displaying measurement result, and a switch unit 15 for power ON operation and for entering personal data such as sex, age and height required to produce whole body fat. In addition, the body fat meter with the weight meter 11 internally includes a weight sensor for detecting body weight, a converter circuit for amplifying and A/D converting the signals from the electrodes 13 and the weight sensor, a memory circuit for storing a body fat estimation function for estimation of whole body fat based upon the whole body impedance and the personal data, an arithmetic circuit for calculating a visceral fat area based upon the data from the converter circuit and the switch unit 15 by using the body fat estimation function stored in the memory unit, and a controller circuit for controlling each of the circuits.

The body fat meter with the weight meter 11 further includes a visceral fat area deriving section comprising: a personal data input unit 4 for entering the personal data such as sex, age and height; a memory unit 5 for storing the regression equation for estimation of the visceral fat area; an arithmetic unit 6 for calculating the visceral fat area based upon the data from the parameter measuring unit 1 and the personal data input unit 4 by using the regression equation for estimation of the visceral fat area stored in the memory unit 5; an evaluation unit 7 for evaluating the health or corpulence condition based upon the result of the visceral fat area produced by the arithmetic unit 6; a display unit 8 for displaying the results from the arithmetic unit 6 and the evaluation unit 7; and a controller unit 9 for controlling each of the units and the entire apparatus for deriving the visceral fat area.

The personal data input unit 4, the memory unit 5, the arithmetic unit 6, the display unit 8 and the controller unit 9 in the visceral fat area deriving section may be used in common with the switch unit, the memory circuit, the arithmetic circuit, the display unit and the controller circuit in the parameter measuring section for measuring whole body fat and body weight.

The encoder type measure 21 corresponds to the parameter measuring unit 1 for measuring girth of an abdomen. It includes, on an external front surface of a housing 22, a display unit 23 for displaying the measurement results, and a switch unit 24 for power ON operation and for entering the personal data such as sex, age, height and race. The encoder type measure 21 further includes a measuring tape 25 wound and loosened into and out of the housing 22 through the sidewall thereof In addition, a size determination unit for detecting the position of the measuring tape loosened, a converter circuit for amplifying and A/ID converting the signal from the size determination unit, an arithmetic circuit for calculating the girth of abdomen based on the signal from the converter circuit, and a controller circuit for controlling each of the circuits are contained within the housing 22.

Figure 13:
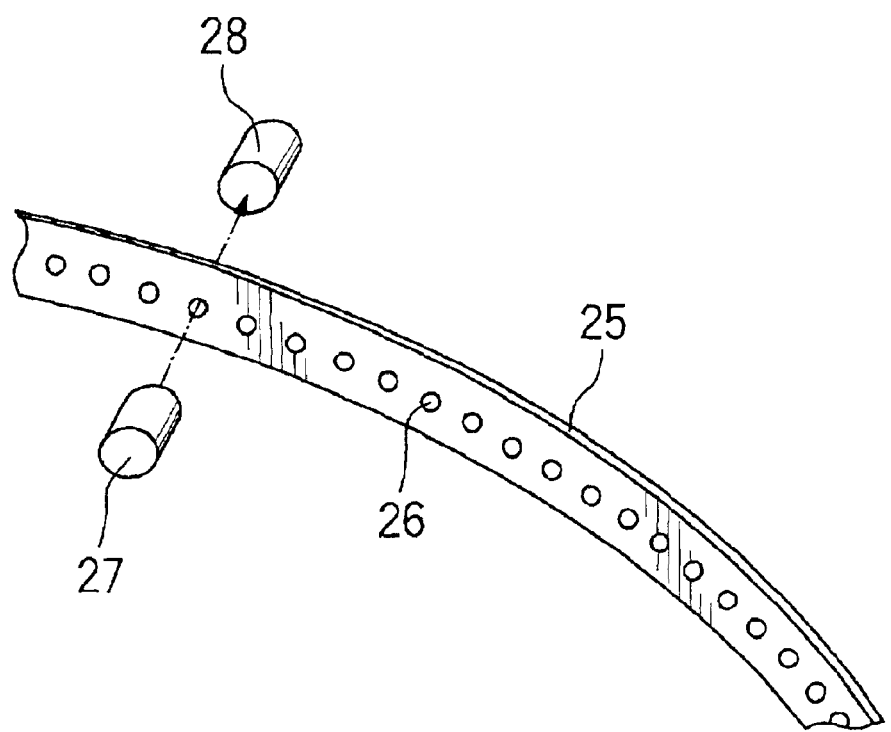
FIG. 13 shows principle of operation of a measuring tape and a size determination unit in an encoder type measure.

Now, principle of operation of the measuring tape 25 and the size determination unit will be described. FIG. 13 shows principle of operation of the measuring tape 25 and the size determination unit in the encoder type measure. The measuring tape 25 has a series of detection holes 26 longitudinally formed at fixed intervals and substantially at the center of the width dimension thereof. The size determination unit has a light emitting element 27 and a light receiving element 28 which are disposed opposite to each other with the measuring tape 25 sandwiched therebetween. The light emitting element 27 and the light receiving element 28 are so positioned that the detection holes 26 in the measuring tape 25 pass across a light beam path for the light emitted by the light emitting element 27 and received by the light receiving element 28. As the measuring tape 25 is loosened the detection holes 26 are moved accordingly. Therefore, the number of holes 26 moved is counted and then it is multiplied by the interval between the holes 26 to produce the length of the tape loosened.

Figure 14:
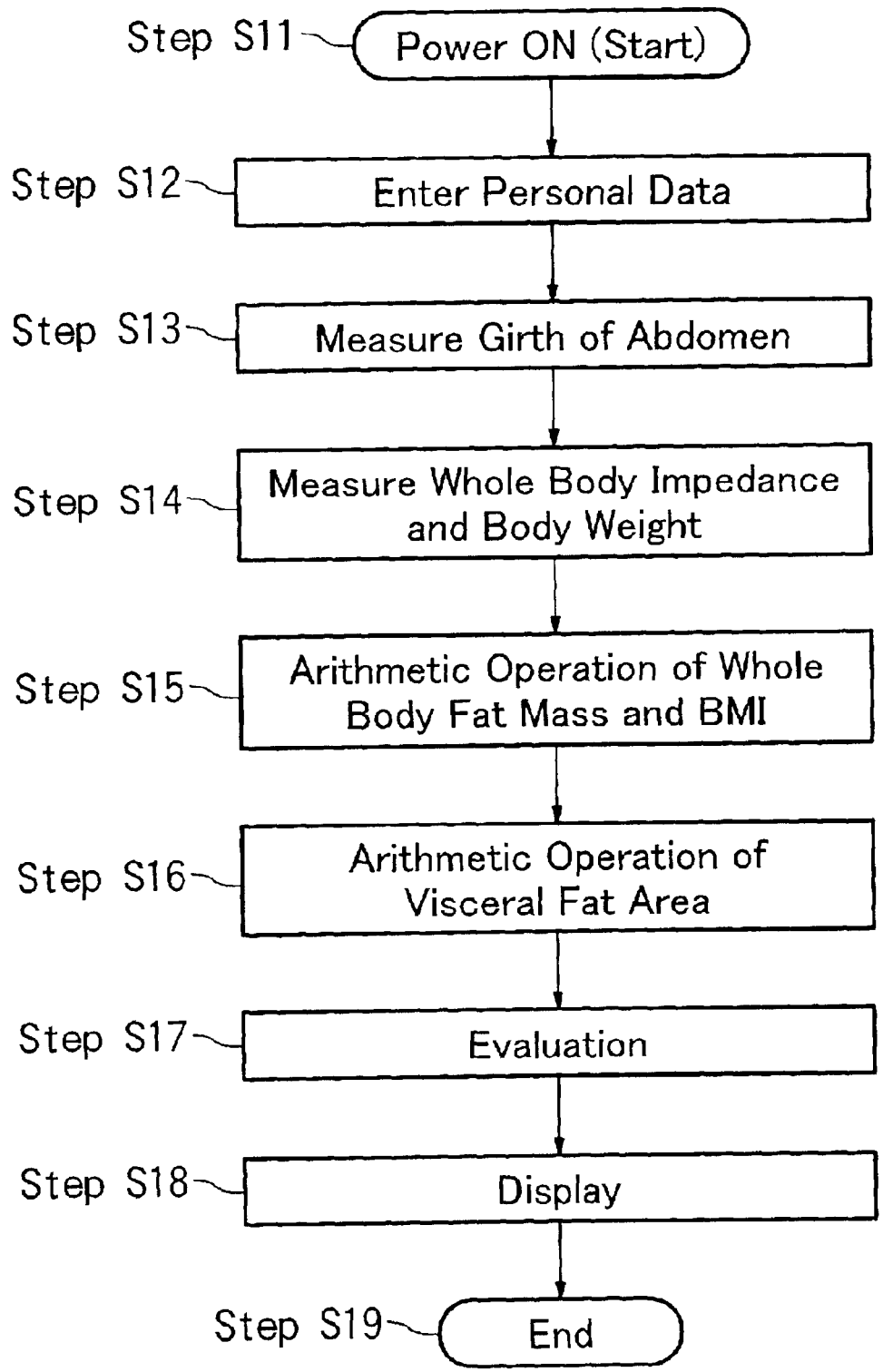
FIG. 14 is a flow chart illustrating a sequence of steps for deriving a visceral fat area in one embodiment.

Now, an operation of the apparatus for deriving the visceral fat area in one embodiment will be described in detail. FIG. 14 is a flow chart illustrating a sequence of steps for deriving the visceral fat area in one embodiment. First of all, the switch unit 15 or 24 of the apparatus for deriving the visceral fat area is turned ON (Step S11). Then, the personal data such as sex, age and height are entered by use of the switch unit 15 or 24 (Step S12). Alternatively, instead of age, the date of birth may be entered. In this case, the current date is read from a timer in the controller circuit and the arithmetic circuit calculates the age according to an equation "age=current date−date of birth".

Next, the person to be measured wraps the measuring tape 25 of the encoder type measure 21 around his abdomen (in particular around his navel region) to measure the girth of abdomen (Step S13). Then, the person to be measured mounts on the body fat meter with the weight meter 11 to measure the whole body impedance and the body weight (Step S14).

The arithmetic circuit then calculates the whole body fat mass and BMI based on the measurement data and the entered data. The whole body fat mass is derived based on the whole body impedance, body weight, sex, age and height data. The BMI is derived based on the body weight and height data (Step S15).

Thereafter, by using the regression equation written by the following equation (2) for estimation of the visceral fat area based on the calculated data of whole body fat mass and BMI, the measured data of girth of the abdomen, and the entered data of age, then the visceral fat area is derived (Step S16).

$$\text{Visceral fat area } Y_1 = a_{58} \times \text{girth of abdomen} + b_{58} \times \text{BMI} + c_{58} \times \text{whole body fat mass} + d_{58} \times \text{age} + f \quad (2)$$

In this connection, if the apparatus is configured to derive visceral fat mass or visceral percent fat, the regression equation written by the following equation (3) or (4) is used:

$$\text{Visceral fat mass } Y_2 = a'_{58} \times \text{girth of abdomen} + b'_{58} \times BMI + c'_{58} \times \text{whole body fat mass} + d'_{58} \times \text{age} + f' \quad (3)$$

$$\text{Visceral percent fat } Y_3 = a''_{58} \times \text{girth of abdomen} + b''_{58} \times BMI + c''_{58} \times \text{whole body fat mass} + d''_{58} \times \text{age} + f' \quad (4)$$

Alternatively the visceral fat mass or visceral percent fat may be derived from the visceral fat area $Y_1$ as derived by using the regression equation (2), as follows:

$$\text{Visceral fat mass } Y_2 \text{ or Visceral percent fat } Y_3 = f(Y_1) \quad (5)$$

Then, the evaluation unit 7 evaluates as to whether the visceral fat area produced by the arithmetic circuit is larger or smaller as compared to certain evaluation criterion (Step S17). The display units 14, 23 display the measured and entered values, the calculated value of the arithmetic circuit and the result of evaluation of the evaluation unit 7 (Step S18). The person to be measured then can see such values and result and the operation is ended (Step S19).

As described above, the apparatus for deriving the visceral fat area according to one embodiment of the present invention operates to measure the parameter values correlated to the visceral fat area, i.e., the whole fat mass, girth of the abdomen and BMI by use of the body fat meter with the weight meter 11 and the encoder type measure 21 (that is the parameter measuring unit 1). Then, the arithmetic circuit or arithmetic unit 6 operates based on the measured parameter values by using the regression equation for estimation of the visceral fat area stored in the memory circuit or memory unit 5 to produce the visceral fat area.

Furthermore, by entering the personal data of age with the switch unit 15 or 24, the parameter values directly correlated to the visceral fat area, i.e., the whole body fat mass, girth of the abdomen and BMI is added the parameter value not directly correlated to the visceral fat area, i.e., the age. Therefore, the arithmetic operation is performed with the regression equation (2) where the coefficient of determination $R^2$ approaches 1, as is apparent by comparison of the coefficient of determination $R^2$ in FIGS. 10 and 11. As the result, the visceral fat area can be derived with higher precision of estimation.

The evaluation unit 7 evaluates as to whether the visceral fat area produced by the arithmetic circuit is larger or smaller as compared to certain evaluation criterion. Therefore, the person to be measured is promptly informed of need to pay attention to his the health or corpulence condition. Furthermore, the display units 14, 23 provide more readable and understandable indication so that the person to be measured is surely be informed of higher need of taking care of his health or corpulence condition.

The body fat meter with the weight meter 11 and the encoder type measure 21 may be connected to each other via wireless means including an infrared ray or low-level electromagnetic wave, instead of a cable.

The encoder type measure 21 is an electronic measurement unit that is made on the basis of a commonly known manual tape measure in which a person reads a scale on the tape for measurement. Therefore, the measurement and communication can be electrically performed without any need of an attendant.

Alternatively the parameter measuring unit 1 for measuring the girth of abdomen may consist of an ultrasonic type measure, instead of the encoder type measure 21. In this case, similar to the encoder type measure 21, the ultrasonic type measure includes a display unit, a switch unit, a measuring tape, a size determination unit, a converter circuit, an arithmetic circuit and a controller circuit. However, the principle of operation of the measuring tape and the size determination unit is different.

Figure 15:
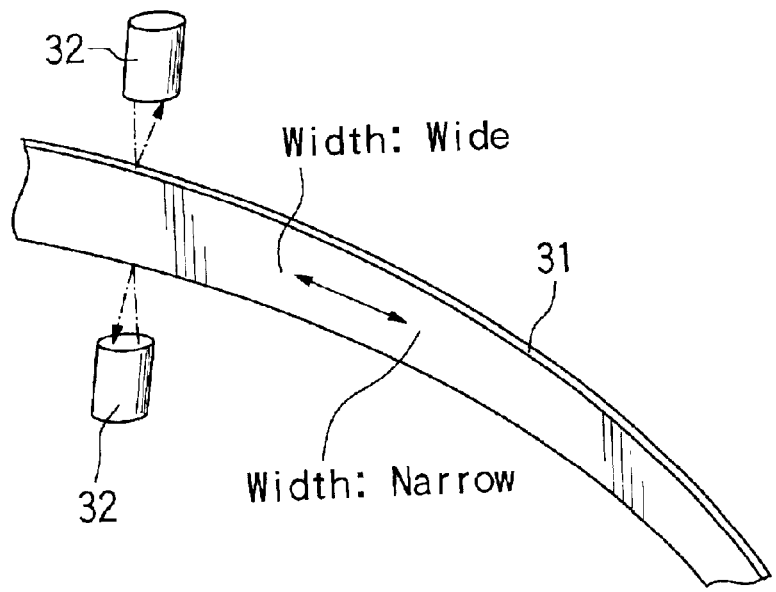
FIG. 15 shows principle of operation of a measuring tape and a size determination unit in an ultrasonic type measure.

FIG. 15 shows principle of operation of a measuring tape and a size determination unit in an ultrasonic type measure. The measuring tape 31 is tapered so that it is reduced in width from the rear end toward the front end. The size determination unit consists of two ultrasonic wave transmitting and receiving elements 32 each of which is disposed opposite to the side edge surface (forming the thickness) of the measuring tape. In this connection only one ultrasonic wave transmitting and receiving element 32 may be used. The ultrasonic wave transmitted by the ultrasonic transmitting and receiving element 32 is incident to the side edge surface of the tape and reflected back. As the measuring tape 31 is loosened its width is gradually changed so that the time period during which the ultrasonic wave is transmitted and reflected back is changed accordingly. Then, by measuring this time period, the length can be determined from the relationship between the time period and the position on the tape 31 loosened.

Figure 16:
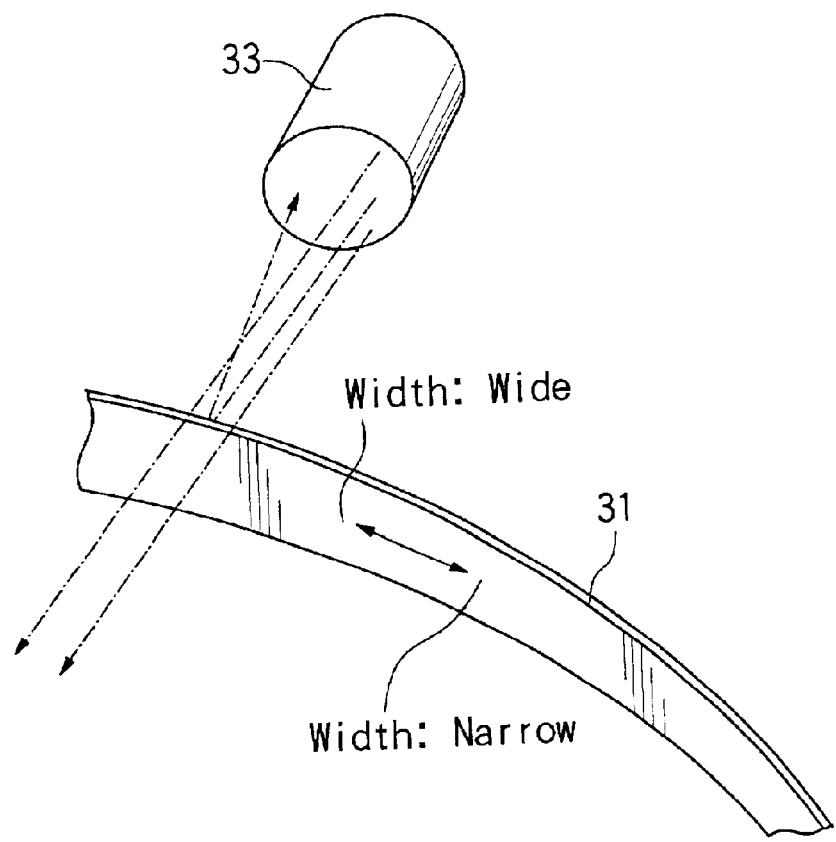
FIG. 16 shows another principle of operation of a measuring tape and a size determination unit in an ultrasonic type measure.

FIG. 16 shows another principle of operation of a measuring tape and a size determination unit in an ultrasonic type measure. The measuring tape 31 is tapered so that it is reduced in width from the rear end toward the front end. The size determination unit consists of an ultrasonic wave transmitting and receiving element 33 that is disposed opposite to one surface of the measuring tape. The width of ultrasonic wave beam transmitted by the ultrasonic transmitting and receiving element 33 is wider than that of the measuring tape. A part of the ultrasonic wave beam transmitted by the ultrasonic transmitting and receiving element 33 is incident to the surface of the tape and reflected back. As the measuring tape 31 is loosened its width is gradually changed so that the amount of ultrasonic wave reflected back is changed accordingly. Then, by measuring the amount of ultrasonic wave reflected back, the length can be determined from the relationship between the amount of ultrasonic wave reflected back and the position on the tape 31 loosened.

Similar to the encoder type measure 21, the ultrasonic type measure may be connected to the body fat meter with the weight meter 11 via wireless means including an infrared ray or low-level electromagnetic wave, instead of a cable. The ultrasonic type measure is an electronic measurement unit that is made on the basis of a commonly known manual tape measure in which a person reads a scale on the tape for measurement. Therefore, the measurement and communication can be electrically performed without any need of attendant.

In one embodiment of the present invention the parameter measuring unit 1 includes the body fat meter with the weight meter 11 as a part thereof, but in another embodiment it may include a body fat meter for deriving the body fat based on the impedance between both hands or an eight-electrode body fat meter for deriving the body fat for each portion of a person such as a hand, a foot or a body.

In one embodiment of the present invention the parameter measuring unit 1 consisting of the body fat meter with the weight meter 11 and the encoder type measure 21 was used as the parameter acquisition means for collecting the parameters on the basis of which the visceral fat area is estimated, but instead a switch or other parameter input unit 2 may be used as the parameter acquisition means. In this case, a converter circuit, a memory circuit, an arithmetic circuit and a controller circuit is contained in a housing like a handheld calculator, and a display unit, a personal data input unit, and a switch or other parameter input unit 2 are mounted on the surface of the housing.

Now, a display format of the display unit that is an essential part of the present invention will be described in detail with reference to FIGS. 17 to 20. The description that will be made hereafter for the display unit may be applied to either of the display unit 14 and 23 of the apparatus as shown in FIG. 5.

Figure 17:
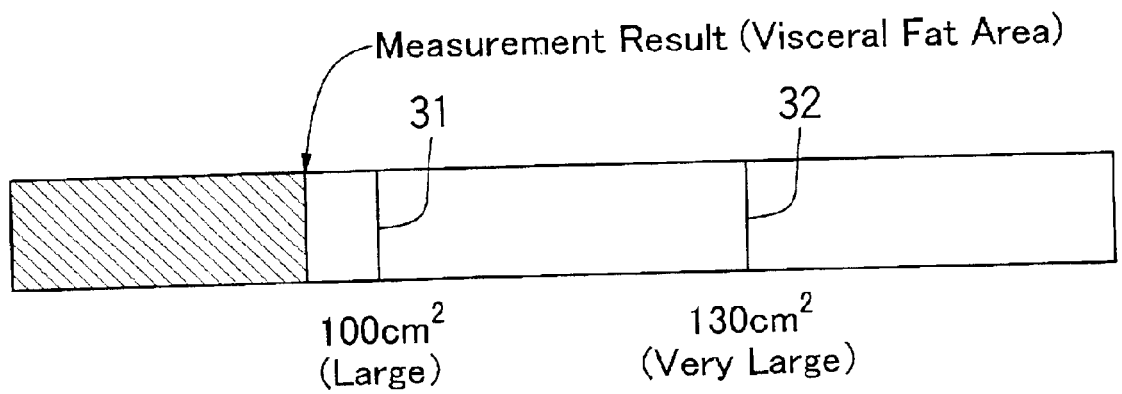
FIG. 17 shows one display format of the present invention.

FIG. 17 shows one display format of the present invention in which the visceral fat area derived is displayed in the form of a bar graph. In this example the bar graph is provided with two threshold lines 31 and 32 as the evaluation criteria in order to determine the visceral fat area derived is good or not. More specifically the threshold line 31 is positioned on the bar graph where the visceral fat area is 100 cm$^2$, which means that the visceral fat area is large, necessitating a diet and an exercise. The other threshold line 32 is positioned on the bar graph where the visceral fat area is 130 cm$^2$, which means that the visceral fat area is very large, necessitating an examination for any disease. Because of the threshold lines 31 and 32 provided in the graph as the evaluation criteria, it becomes possible for a person to be measured to visually understand how much is the visceral fat area larger or smaller as compared to the evaluation criteria. Therefore, the person to be measured can easily and promptly know his own health condition. In addition, because the threshold lines for evaluating the visceral fat area are positioned progressively on the graph or at the level of 100 cm$^2$ and 130 cm$^2$, the person to be measured can be given stronger impact about the measurement result. In this connection, the visceral fat area of 100 cm$^2$ and 130 cm$^2$ at which the threshold lines are positioned in this example corresponds to the evaluation criterion as published by Japan Society for the Study of Obesity.

Figure 18:
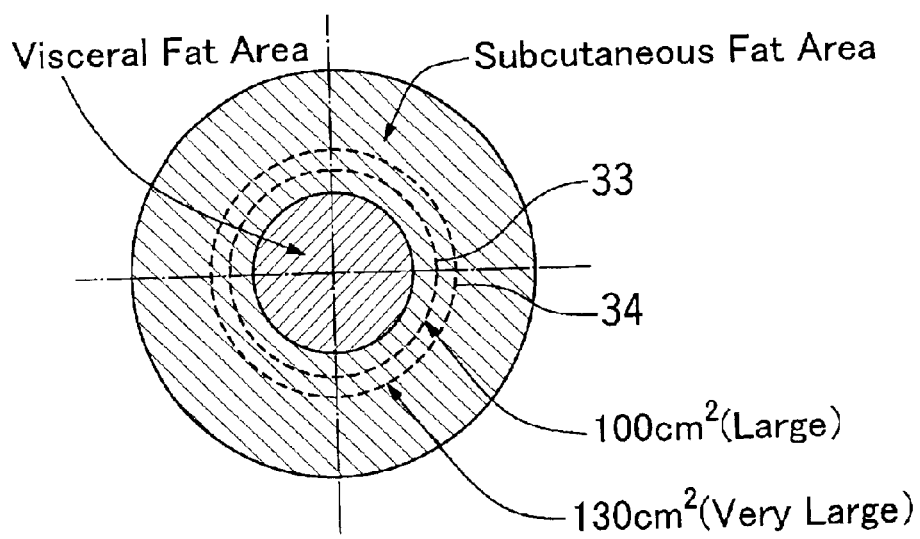
FIG. 18 shows another display format of the present invention.

FIG. 18 shows another display format of the present invention in which the gross fat area at the outside and the visceral fat area at the inside are displayed using concentric circles. A portion produced by subtracting the inside circle from the outside circle corresponds to the subcutaneous fat area. For the visceral fat area that has significant effect on the health the threshold circles 33 and 34 are concentrically provided as the evaluation criteria at the positions corresponding to the visceral fat area of 100 cm$^2$ (which means that the visceral fat area is large, necessitating a diet and an exercise) and 130 cm$^2$ (which means that the visceral fat area is very large, necessitating an examination for any disease). Similar to the bar graph of FIG. 17, the person to be measured can visually understand how much is the visceral fat area larger or smaller as compared to the evaluation criteria and the person to be measured can be given stronger impact about the measurement result. In addition, the person to be measured can visually understand the amount of gross fat area and the ratio of visceral fat area to subcutaneous fat area, and therefore, can easily and promptly know his own health condition.

Figure 19:
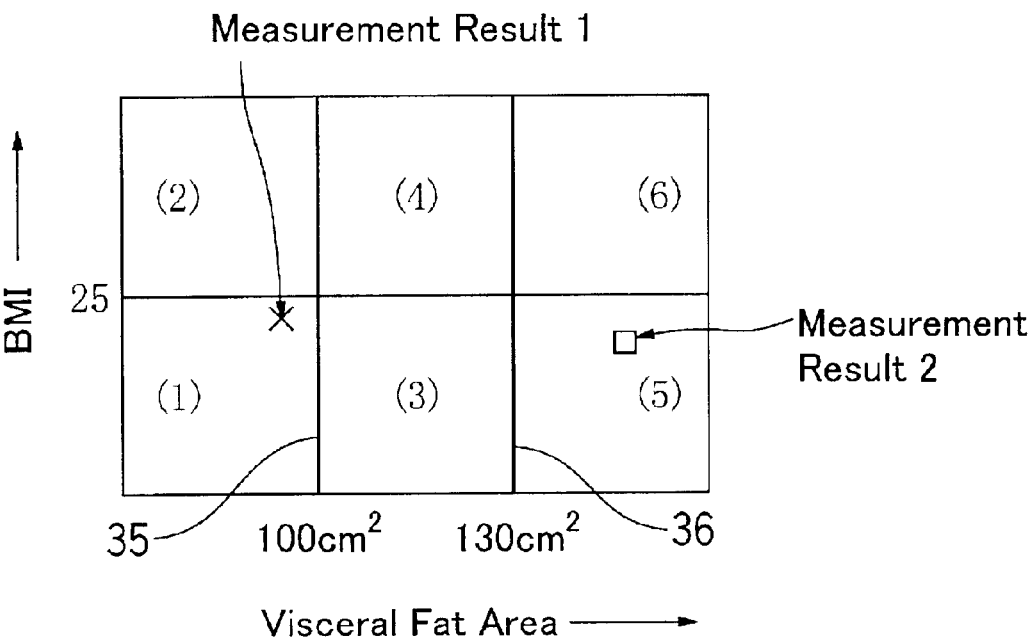
FIG. 19 shows further display format of the present invention.

FIG. 19 shows further display format of the present invention in which the measurement result is positioned at the corresponding point within a matrix-like graph that plots BMI selected from corpulence evaluation indexes (that are formed from the ratio of body weight to height and including BMI, Kaup index and Rohrer index) on an ordinate and plots the visceral fat area on an abscissa of the graph. The threshold lines 35 and 36 are successively provided as the evaluation criteria on the abscissa of the graph at the positions corresponding to the visceral fat area of 100 cm$^2$ and 130 cm$^2$. Another threshold line 37 is provided as the evaluation criterion for BMI on the ordinate of the graph at the position corresponding to BMI of 25. This evaluation criterion of 25 for BMI is one that is published by Japan Society for the Study of Obesity. Because of the graph having the evaluation criteria for the measurement result in regard to the relationship between the visceral fat area and other living body information or BMI, more information for evaluation of the health can visually be understood from the graph. More specifically, if the measurement result is present in the region (1) or (2) of the graph, it means that the health is in good condition. However, if the measurement result is present in the region (3), the health is not good, indicating that there is a need of keeping in mind of an exercise and suppressing any excessive intake of sugar and fat. If the measurement result is present in the region (4), the health is in bad condition, indicating that there is a need of active exercise and of reduction in body weight by calorie limitation. If the measurement result is present in the region (5), the health is very bad, indicating that there is a need of active exercise and diet. Finally, if the measurement result is present in the region (6), the health is very bad, indicating that there is a need of periodical health control by an expert person. In an alternative embodiment an additional threshold line may be provided on the ordinate of the graph as an additional evaluation criterion for BMI. Any number of the threshold lines may be provided on the abscissa and the ordinate of the graph according to the intended application.

Figure 20:
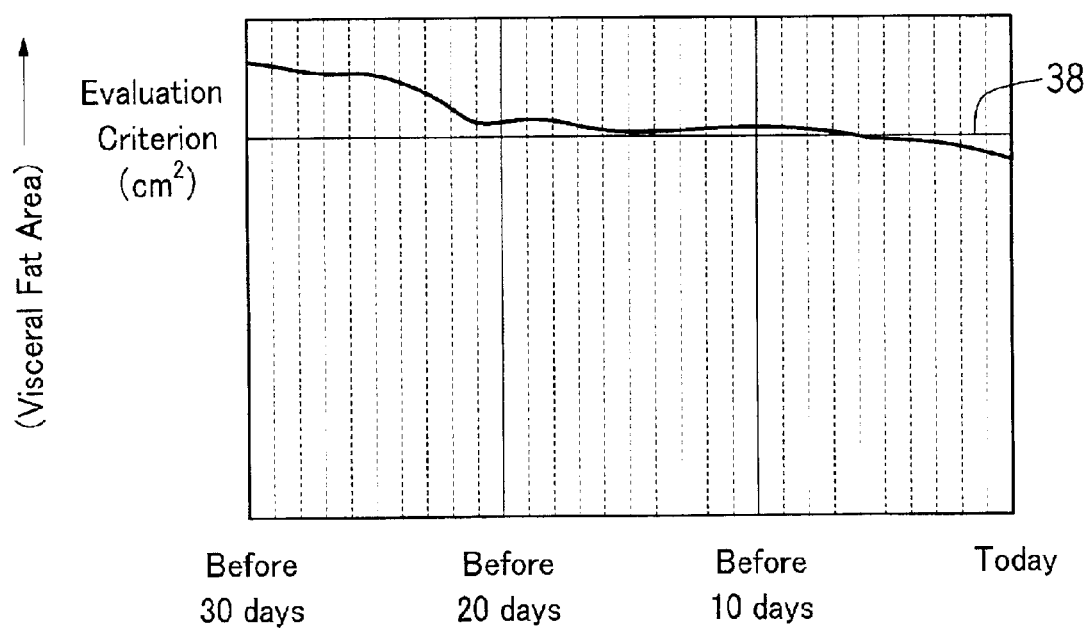
FIG. 20 shows yet further display format of the present invention.

FIG. 20 shows yet further display format of the present invention in which the measurement result derived up to now is historically displayed in a line graph that plots the visceral fat area on an ordinate and the time on an abscissa of the graph. In this graph the threshold line 38 is provided as the evaluation criterion under which the visceral fat area is good. Any tendency that the measurement result in the past exhibits relative to the evaluation criterion can be visually understood about whether it is temporal or permanent. Therefore, a person to be measured can properly understand his current health condition.

In the embodiments as shown in FIGS. 17 to 20 the shape, color, figure, marking, hue and flashing condition may be changed every time when the measurement result exceeds each of the threshold lines. For example, in the embodiment of FIG. 17, the portion of the graph representing the measurement result may be changed in color from "blue" to "yellow" and hence to "red" every time when the measurement result exceeds the threshold lines at 100 $cm^2$ and 130 $cm^2$. In the embodiment of FIG. 19 the measurement result may be indicated by either one of circle, triangle, rectangle, cross and star marks depending upon to which of the regions the measurement result belongs. Thus the visual understanding of the measurement result becomes more easier.

In addition, an advice information for the measurement result may be given in the form of a message. For example, in the embodiment of FIG. 17, a message such as "A diet and an exercise are necessary" or "An examination for disease is necessary" may be displayed in a comment window on the display unit every time when the measurement result exceeds each of the threshold lines at 100 $cm^2$ and 130 $cm^2$ on the graph. In the embodiment of FIG. 19, if the measurement result belongs to the region (1) or (2) of the graph, a message such as "Continue the current living condition" may be displayed in a comment window "A" corresponding to the measurement result 1 in FIG. 19. But, if the measurement result belongs to the region (3) of the graph, a message such as "Do an exercise and take care of not to intake excessive sugar and fat" may be displayed. If the measurement result belongs to the region (4) of the graph, a message such as "Do an exercise actively and reduce the body weight by calorie limitation" may be displayed. If the measurement result belongs to the region (5) of the graph, a message such as "Do an exercise actively and limit to take the food including sugar and fat" may be displayed. Finally if the measurement result belongs to the region (6) of the graph, a message such as "Have a periodical health control by a physician" may be displayed. Thus a person to be measured can see what is necessary in his every day life.

Alternatively, as shown in a comment window "B" corresponding to the measurement result 2 in FIG. 19, a plurality of selectable instructions for an exercise may be displayed. In this case, the person to be measured may select any one of the exercise instructions that is suitable for him, which can surely guide the person to be measured toward such condition that he has a proper visceral fat area. The reason for which is that the exercise instructions in the comment window "B" are such advice information that have been generally used for reducing the body weight (the advice information is changed depending upon the amount of body weight to be reduced). In this connection, it is noted that BMI is calculated based on the relation between height and body weight, and because of the height generally kept constant, reducing the body weight causes reduction of BMI as well. In addition, because of the visceral fat area having higher correlation with BMI (an experiment has shown the correlation factor of 0.79), as BMI is reduced the visceral fat area is reduced as well. Accordingly, for the measurement result 2 in FIG. 19, each of the exercise instructions in the window "B" means the advice information for reducing the body weight in order to bring the visceral fat area belonging to the region in question to the proper value. In alternative embodiment the plurality of the exercise instructions may be displayed in the comment window "B" of the display unit one at a time, and it may be scrolled every time a switch is depressed.

In the embodiment as described above, the threshold for the visceral fat area of 100 $cm^2$ and 130 $cm^2$, as published by Japan Society for the Study of Obesity, was used as the evaluation criteria. However, the present invention is not limited to such values, and any other evaluation criteria using words such as "normal", "large" and "very large" may be used, instead of the numerical value.

In the embodiment as described above, in order to derive the body fat area, the parameter measuring unit 1 was used to measure the parameter value correlated to the body fat area, and the personal data input unit 4 was used to enter the personal data such as sex, age and height. In an alternative embodiment, however, a parameter input unit may be used, instead of the parameter measuring unit 1, or a parameter input unit may additionally be used in order to enter the parameter value correlated to the body fat area. Furthermore, a personal data measuring unit may be used, instead of the personal data input unit 4, or a personal data measuring unit may additionally be used in order to measure the personal data such as sex, age and height. Such alternative embodiment can equally attain the same purpose of deriving the body fat area.

It is apparent from the foregoing that according to the present invention a person to be measured knows not only a body fat mass and percent fat of a whole body, but also he can easily measure by himself a body fat area including visceral fat area and subcutaneous fat area by use of a small and cheap apparatus without any exposure to X-ray.

Because an evaluation is made as to whether the measured value of the visceral fat area is larger or smaller as compared to certain evaluation criterion and the result of evaluation is displayed, the person to be measured can be given an effective information necessary for health care.

By taking into consideration of a personal data, the body fat area can be estimated with higher precision, and thus, a reliable information can be provided.

Because a conventional tape measure in which a person read a scale on the tape for measurement is replaced with an encoder type or ultrasonic type measure for measuring a girth of an abdomen, the measurement data can be communicated without any need of attendant, which further facilitates the measurement operation.

Furthermore, according to the present invention, a person to be measured can see not only the measurement result of body fat area, but also can visually understand as to whether the measurement result is good for health or not, and additionally, can be given an advice information representing what action should be taken for the health care. Therefore, instead of simply deriving the value of body fat area, the result of the body fat area derived can easily and effectively be utilized for health care.

What is claimed is:

1. An apparatus for deriving a body fat area comprising:
   a parameter measuring unit and/or a parameter input unit;
   a memory unit;
   an arithmetic unit; and
   a displaying unit;
   wherein said parameter measuring unit measures a parameter value correlated to the body fat area including at least a visceral fat area and a subcutaneous fat area, and said parameter input unit enters a parameter value correlated to the body fat area,
   said memory unit stores a regression equation for estimation of the body fat area;
   said arithmetic unit calculates the body fat area, including the subcutaneous fat area and the visceral fat area, based on said parameter values from said parameter measuring unit and/or said parameter input unit by using said regression equation for estimation of the body fat area stored in said memory unit; and
   said display unit displays said calculated subcutaneous fat area and said calculated visceral fat area in a display format in which the subcutaneous fat area and the visceral fat area are represented using concentric circles in a graphical display, the visceral fat area being represented at an inside portion of the graphical display, and the subcutaneous fat area being represented at an outside portion of the graphical display.

2. An apparatus for deriving a body fat area according to claim 1 further comprising a personal data input unit and/or a personal data measuring unit, wherein said personal data input unit enters a personal data including at least one of sex, age and height, and said personal data measuring unit measures a personal data including at least one of sex, age and height, and
   said arithmetic unit takes into consideration the personal data from said personal data input unit and/or said personal data measuring unit.

3. An apparatus for deriving a body fat area according to claim 1 or 2 in which said display unit further displays threshold lines as evaluation criterion.

4. An apparatus for deriving a body fat area according to claim 3 in which said threshold lines are successively provided.

5. An apparatus for deriving a body fat area according to claim 4 in which a display pattern is changed for each of the regions defined by said threshold lines.

6. An apparatus for deriving a body fat area according to claim 5 in which said display pattern is formed by shape, color, figure, marking, hue or flashing condition.

7. An apparatus for deriving a body fat area according to claim 3, in which said evaluation criterion includes concentric threshold lines provided on the positions where the visceral fat area is 100 cm$^2$ and 130 cm$^2$.

8. An apparatus for deriving a body fat area according to claim 1 or 2 in which said parameter correlated to the body fat area is at least one of trunk segment fat, whole body fat, whole body impedance, BMI, kaup index and Rohrer index.

9. An apparatus for deriving a body fat area according to claim 8 in which said trunk segment fat is a trunk segment body fat rate or an amount of trunk segment body fat.

10. An apparatus for deriving body fat area according to claim 9 in which said whole body fat is a whole body fat rate or an amount of whole body fat.

11. An apparatus for deriving a body fat area, comprising:
    a parameter measuring unit and/or a parameter input unit;
    a memory unit;
    an arithmetic unit; and
    a display unit,
    wherein said parameter measuring unit measures a parameter value correlated to the body fat area, and said parameter input unit enters a parameter value correlated to the body fat area,
    said memory unit stores a regression equation for estimation of the body fat area,
    said arithmetic unit calculates the body fat area based on said parameter values from said parameter measuring unit and/or said parameter input unit by using said regression equation for estimation of the body fat area stored in said memory unit, and
    said display unit displays the result of said calculation in a matrix-like graph that plots a corpulence evaluation index on an ordinate and plots a body fat area on an abscissa of the graph.

12. An apparatus for deriving a body fat area according to claim 11 in which said body fat area is a visceral fat value or a subcutaneous fat value or a gross fat value.

13. An apparatus for deriving body fat area according to claim 12 in which said corpulence evaluation index is BMI or kaup index or Rohrer index.

14. An apparatus for deriving body fat area according to claim 13 in which said parameter correlated to the body fat area is at least one of trunk segment fat, whole body fat, whole body impedance, BMI, kaup index and Rohrer index.

15. An apparatus for deriving a body fat area according to claim 14 in which said trunk segment fat is trunk segment body fat rate or an amount of trunk segment fat.

16. An apparatus for deriving a body fat area according to claim 15 in which said whole body fat is whole body fat rate or an amount of whole body fat.

17. An apparatus for deriving a body fat area according to claim 11 in which display unit further displays threshold lines as evaluation criterion.

18. An apparatus for deriving a body fat area according to claim 17 in which said threshold lines are successively provided.

19. An apparatus for deriving a body fat area according to claim 17 or 18 in which said body fat area is a visceral fat area, and said evaluation criterion includes threshold lines provided on the positions where the visceral fat area is 100 cm$^2$ and 130 cm$^2$.

* * * * *